United States Patent [19]

Iwanaga et al.

[11] Patent Number: 4,457,161
[45] Date of Patent: Jul. 3, 1984

[54] GAS DETECTION DEVICE AND METHOD FOR DETECTING GAS

[75] Inventors: Shoichi Iwanaga, Yokohama; Nobuo Sato, Yokosuka; Akira Isegami, Yokohoma; Tokio Isogai, Fujisawa; Takanobu Noro; Hideo Arima, both of Yokohama, all of Japan

[73] Assignee: Hitachi, Ltd., Tokyo, Japan

[21] Appl. No.: 366,304

[22] Filed: Apr. 7, 1981

[30] Foreign Application Priority Data

Oct. 9, 1980 [JP] Japan ................................ 55-140470

[51] Int. Cl.³ .......................................... G01N 27/12
[52] U.S. Cl. ........................................ 73/23; 340/634
[58] Field of Search ................ 73/23, 27 R; 324/71.5; 340/634; 422/98; 338/34

[56] References Cited

U.S. PATENT DOCUMENTS 4,164,862  8/1979  Jackson ............................. 73/27 R
4,338,281  7/1982  Treitinger et al. ................. 73/27 R

FOREIGN PATENT DOCUMENTS 80192  6/1975  Japan .

*Primary Examiner*—Stephen A. Kreitman
*Assistant Examiner*—John E. Chapman, Jr.
*Attorney, Agent, or Firm*—Antonelli, Terry & Wands

[57] ABSTRACT

A gas detection device and a method for detecting a gas where gas information including concentrations of gas components in a mixed gas, concentration, presence of specific gas components and the like is detected by measuring, e.g., the output voltages of a plurality of gas sensors having different gas selectivities. The gas selectivities, as a characteristic constant of the specific gas sensor, was previously determined. The measured output voltages and gas selectivities are then used for solving plural simultaneous equations for gas concentrations.

21 Claims, 18 Drawing Figures (a)

(b)

(a)

(b)

(a)

(b)

GAS DETECTION DEVICE AND METHOD FOR DETECTING GAS

BACKGROUND OF THE INVENTION

1. Field of the Invention

This invention relates to a gas detection device for a mixed gas, which can determine gas information including kinds and concentrations of gas components in a mixed gas consisting of a plurality of known components.

2. Description of the Prior Art

Semiconductor gas sensors such as tin oxide ($SnO_2$), iron oxide ($Fe_2O_3$), and zinc oxide ($ZnO$) can detect gas concentrations in the form of intensities of electrical signal as outputs and are handled with ease and are manufactured at a low cost, and thus they have been widely used so far. Their working principle is such that a change in resistance of a semiconductor gas sensor by adsorption of a sample gas onto the active part of the sensor is determined in the form of a voltage output by a detection circuit, one example of which is shown in FIG. 1, where numeral 11 is a fixed resistor, 12 a $\alpha$-$Fe_2O_3$ based sensor for detecting isobutane ($C_4H_{10}$) and 13 a voltmeter.

Relations between the detected gas concentration and the detected voltage are usually linear in some region, as shown by typical detection characteristics 21 of isobutane ($C_4H_{10}$) obtained by $\alpha$-$Fe_2O_3$ based sensor in FIG. 2, and thus are well applicable to practical measurement.

More specifically, reference will be made to the prior art, where water vapor concentration and alcohol vapor concentration are separately detected at the same time in a mixed gas of air, water vapor and alcohol vapor, as has been so far thoroughly studied. For example, Japanese Laid-Open patent application No. 80192/75 discloses that a few species of sensor materials are required for simultaneous but independent detection of a plurality of gas components, and also a plurality of sensors are required for detection of only one species of gas component, if no sensor is available for detecting only such a species of gas component. In particular, this patent document discloses that, in the latter where no sensor is available for detection of only one species of gas component, for example, when it is desired to detect a gas component a but no sensor is available for detecting only the gas component a and only a sensor A sensitive to both gas components a and b is available, a sensor sensitive not to the gas component a but to the gas component b is prepared to ascertain that there is no gas component b, thereby enabling the sensor A to detect the gas component a. The said Japanese Laid-open patent application discloses that changes in resistances of lanthanum-nickel oxide material ($LaNiO_3$) and magnetite material ($Fe_3O_4$) are calibrated against mixed gases having known concentrations in advance, thereby detecting individual gases in a mixed gas of air, water vapor and alcohol vapor having unknown concentrations.

However, the said gas sensor of the prior art type fails to satisfy the social needs for separation and quantitative determination of a mixed gas, as recently encountered in detection of automobile exhaust gas and chemical plant leak gas. For example, as shown by the detection characteristics of zinc oxide ($ZnO$) based sensor doped with palladium as a $H_2$ gas sensor in FIG. 3, such a sensor detects the output voltage by $H_2$ (characteristic curve 31 in FIG. 3), as well as that by carbon monoxide ($CO$) (characteristic curve 32 in FIG. 3) and that by hydrocarbon gas (propane gas, characteristic curve 33 in FIG. 3) at the same time, and thus the detection accuracy of $H_2$ by such a sensor is considerably lowered. This seems due to adsorption of other gas components than $H_2$ giving a change to $H_2$ adsorption, and this phenomenon usually appears in any gas sensor material as a large disadvantage of the conventional semiconductor gas sensor.

SUMMARY OF THE INVENTION

An object of the present invention is to provide a low cost mixed gas concentration detection device free from the said disadvantage of the prior art, which can precisely and rapidly detect gas information including species of gas components in a mixed gas of known gas components, presence of specific gas components, their concentration, etc.

Another object of the present invention is to provide a low cost, mixed gas concentration detection device free from the said disadvantage of the prior art, which has a function to rapidly detect species of gas components in a mixed gas of known gas components, presence of specific gas components, their concentration and the like, and to highly accurately compute concentrations of gas components from the thus obtained gas information.

The gist of the present invention resides in determining gas information including concentrations of gas components in a mixed gas, concentration ratio, presence of specific gas components and the like by measuring the sensitivities of individual gas sensors to individual gas components in advance by intentionally utilizing the linearity of displayed values of concentrations of gas components to mixing ratios of a mixed gas (the displayed value being a value on calibration curve characteristic) and differences in gas sensitivities to gas components between gas sensor materials, and solving plural simultaneous linear equations set up from the measured determined outputs from the individual sensors and the known sensitivities of the individual sensors to the individual gas components. The relative sensitivities of a gas sensor to identical quantities of the gas components will be hereinafter referred to as "gas selectivity".

DESCRIPTION OF THE PREFERRED EMBODIMENTS

Figure 3:
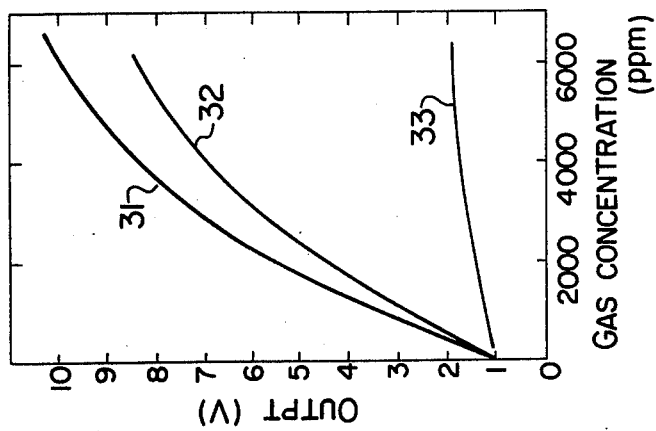
FIG. 3 is a diagram showing one example of detected output characteristics of hydrogen and other gas components by the conventional zinc oxide ($ZnO$) based hydrogen sensor further doped with Pd.
Figure 2:
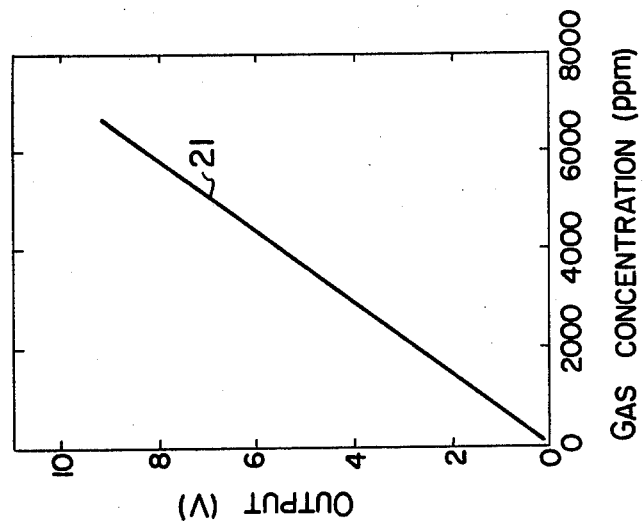
FIG. 2 is a diagram showing one example of characteristics between the gas concentration and the detected voltage according to the detection circuit of FIG. 1.
Figure 1:
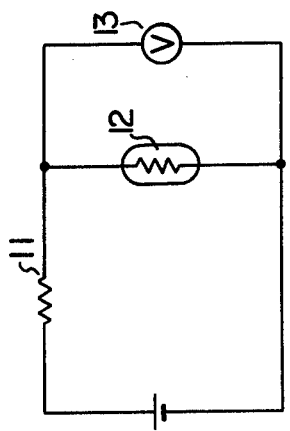
FIG. 1 is a detection circuit diagram for the conventional $\alpha$-$Fe_2O_3$ based gas sensor.

Before describing the embodiments of the present invention, the technical concept of the present invention will be briefly described below to facilitate understanding of the present invention.

Basic technical concept of the present invention is to utilize the fact that contribution of the individual gas components to detected output is substantially additive. That is, suppose that the number of components in a sample mixed gas be n, the detection sensitivity of a gas sensor i to a specific gas component j be $\alpha_{ij}$, and the concentration of component j be $x_j$. Detected output voltage $P_i$ by sensors i, generated by total gas components, can be represented by the following formula:

$$P_i = \sum_{j=1}^{n} P_{ij}$$

$$= \sum_{j=1}^{n} \alpha_{ij} x_j$$

$$(i: 1, 2, \ldots m)$$

where $P_{ij}$ is an output generated from single gas sensor i due to a specific gas component j, $\alpha_{ij}$ is dependent on the gas sensor material, and once a specific sensor material is determined, a detected output must be calibrated against single gas component j. m is the number of gas sensors.

The present inventors have found that such additive nature is valid, and the present invention is based on such finding.

The conventional gas sensor is basically arranged to use gas sensor elements, each being specifically developed to exhibit a greatly larger value of $\alpha_{ij}$ with respect to a specific gas component j while suitably calibrating the effects of other gas components as an error, thereby obtaining an approximate value for the concentration of the specific gas component. On the other hand, in the present invention, each of the gas sensor elements provide an output characteristic which may have a relatively large value of $\alpha_{ij}$ for a specific gas component, as well as having an output characteristic of other gas components, the effects of the other gas components being cancelled by using output characteristics of other gas sensor elements with respect to the other gas components.

A gas concentration $x_j$ can be obtained from the foregoing formula in the same manner as a solution is obtained from well known plural simultaneous linear equations. That is, a group of the same number n of gas sensors, each consisting of different material, as the number of gas components, is exposed to a mixed gas of n gas components to obtain outputs each from the individual sensors, and the individual gas component concentrations $x_j$ are obtained uniquely from these detected outputs by determinant computation. Furthermore, the computation is carried out by a microcomputer that has memorized the sensitivity $\alpha_{ij}$ as constant in advance, and thus the gas concentration can be obtained by means of real time processing.

The basic technical concept of the present invention is thus to intentionally utilize a gas sensitivity to a plurality of gas components of gas sensor material in contrast to the conventional concept of the prior art and thus is unique in this respect.

One embodiment of the present gas detection device will be described in detail below, referring to the drawings.

Figure 4:
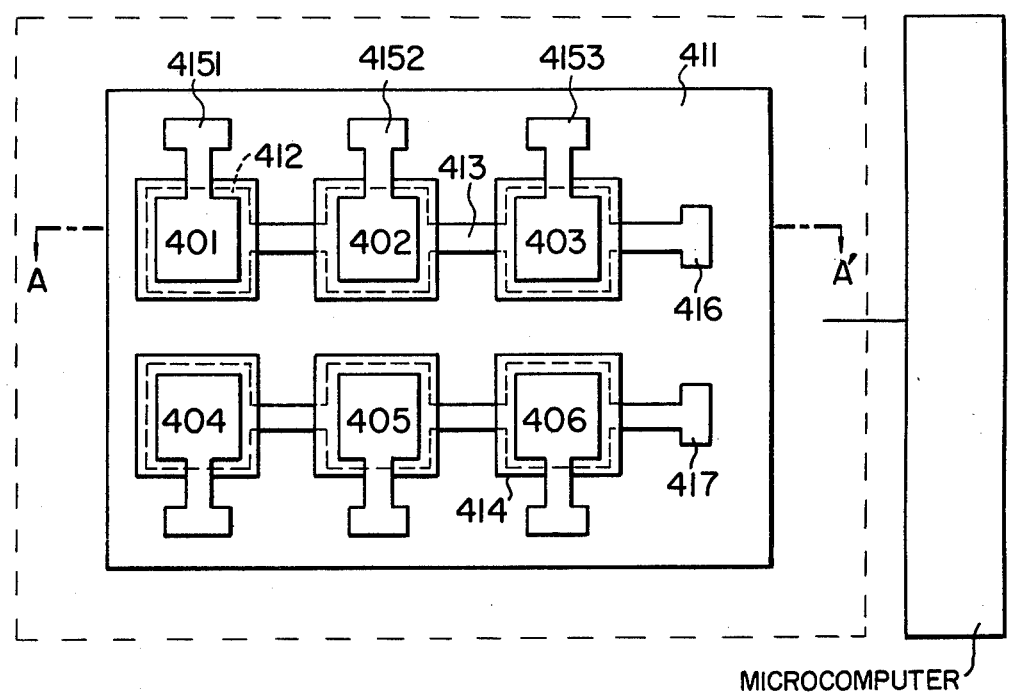
FIG. 4(a) is a schematic view showing the essential part of a first embodiment according to the present invention where 6 sensors are arranged.
FIG. 4(b) is a schematic cross-sectional view of FIG. 4(a) along the line A—A'.
Figure 4:
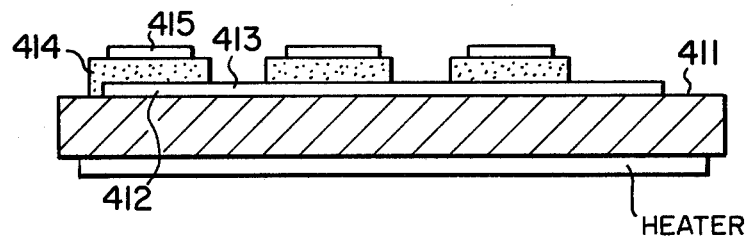

FIG. 4(a) is a schematic view showing a gas sensor section, which is the essential part of the present gas detection device. The gas sensor section has 6 sensors 401, 402, 403, 404, 405 and 406 arranged in a matrix configuration on a substrate 411. The individual sensors are manufactured by forming 6 bottom electrodes 412 from a gold conductive paste (for example, DuPont No. 8760 paste) at predetermined positions according to the well known thick film printing process, and also forming connecting conductors 413 to the bottom electrodes 412, then forming gas sensitive parts by using 6 kinds of gas sensor pastes 414, having different sensitivities to the respective bottom electrodes 412 to a predetermined thickness (about 10 μm) according to the same thick film printing process as applied to the formation of the bottom electrodes 412, then forming top electrodes 415 of predetermined shape and size onto the gas sensors by printing process, and firing the entire sensors at a firing temperature of 900° C. for 10 minutes. Thus, a sensor assembly for analyzing a plurality of gas components having a sandwich configuration for the individual sensors and having predetermined wirings can be obtained.

In realizing the foregoing embodiment according to the technical concept of the present invention, 6 kinds of sensor paste materials are used. That is, a CoO-based material is used for sensor 401, $WO_3$+Pt-based material for sensor 402, $VO_2$+Ag-based material for sensor 403, ZnO+Pd-based material for sensor 404, $Fe_3O_4$-based material for sensor 405, and $SnO_2$-based material for sensor 406, the individual materials being admixed with about 10% by weight of high melting point crystal glass and also with an organic binder and kneaded thoroughly to provide the sensor pastes.

Signals (voltage output) from the gas sensor section of such a structure as described above are taken out through combinations of top electrodes 415 and bottom electrodes 412. For example, the signal from sensor 402 can be obtained by selecting the output terminal of the bottom electrode 416 in the first line group and the output terminal of the top electrode 4152 at the second row group. As the whole, the signals are obtained by scanning of individual electrodes in the line group and at row group, as described above.

FIG. 4(b) is a schematic cross-sectional view of the structure along line A—A' of FIG. 4(a).

FIGS. 5-10 are diagrams showing characteristics of detected output voltages of sensors 401–406 in the sensor section as the essential part of a gas detection device for a mixed gas of oxygen, hydrogen, nitrogen dioxide, carbon monoxide, hydrocarbon and water vapor.

Figure 5:
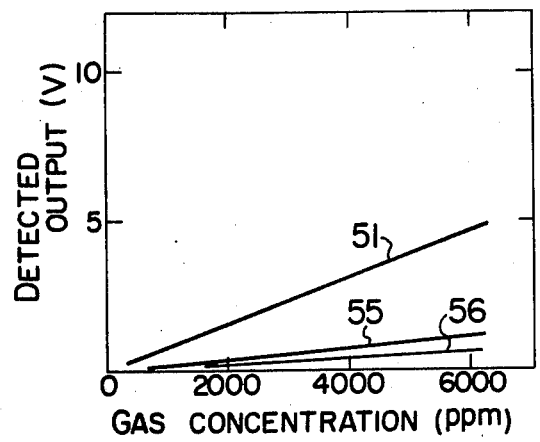
FIGS. 5–10 are characteristic diagrams showing detected outputs for a mixed gas of six gas components by 6 sensors according to the first embodiment of FIG. 4.

In FIG. 5, line 51 shows characteristics of detected output by the CoO-based gas sensor for oxygen ($O_2$), line 55 for water vapor ($H_2O$), and line 56 for hydrocarbon.

Figure 6:
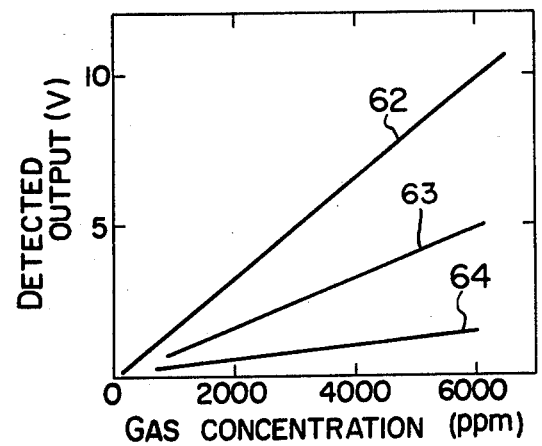

In FIG. 6, line 62 shows characteristics of detected output by the $WO_3$+Pt-based gas sensor for hydrogen ($H_2$), line 63 for nitrogen dioxide ($NO_2$), and line 64 for carbon monoxide (CO).

Figure 7:
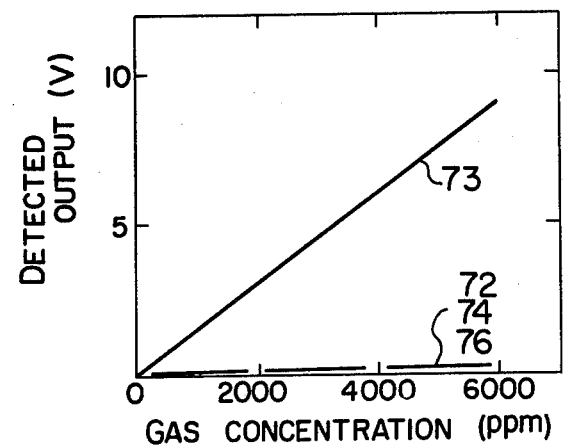

In FIG. 7, line 72 shows characteristics of detected output by the VO$_2$+Ag-based gas sensor for H$_2$, line 73 for O$_2$, line 74 for CO, and line 76 for hydrocarbon.

Figure 8:
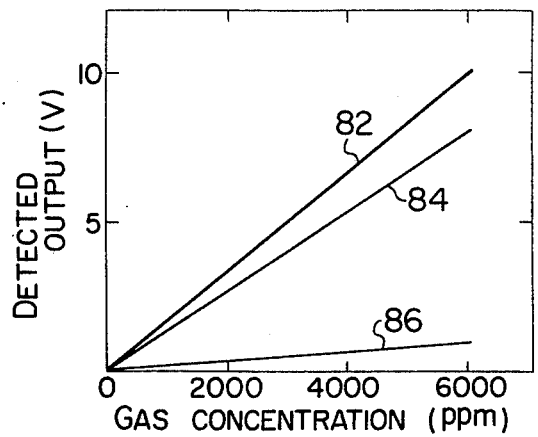

In FIG. 8, line 82 shows characteristics of detected output by the ZnO+Pd-based gas sensor for H$_2$, line 84 for CO, and line 86 for hydrocarbon.

Figure 9:
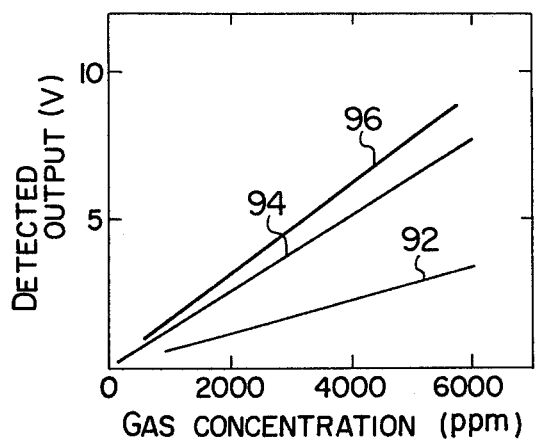

In FIG. 9, line 92 shows characteristics of detected output by the SnO$_2$-based gas sensor for H$_2$, line 94 for CO, and line 96 for hydrocarbon.

Figure 10:
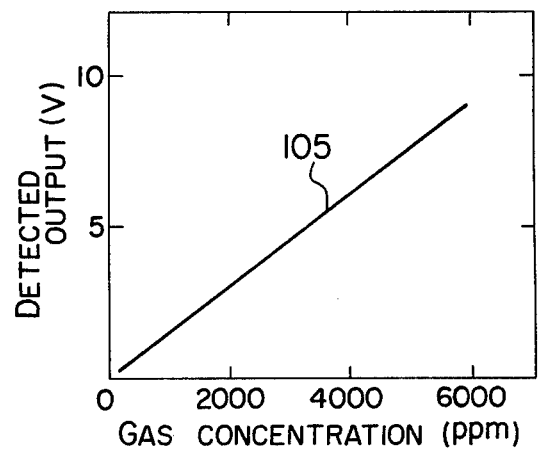

In FIG. 10, line 105 shows characteristics of detected output by the Fe$_3$O$_4$-based gas sensor for H$_2$O (gas).

The gas sensor assembly is used for detection while heating the sensor materials, generally at 400°–450° C., although the heating temperature ranges as shown in the following Table 1 are regarded as optimum for the individual sensor materials. A sheet form heater having a good temperature distribution is used as a heater.

TABLE 1

| Optimum heating temperature for individual sensor materials | |
| --- | --- |
| CoO-based gas sensor | 400°–500° C. |
| WO$_3$ + Pt-based gas sensor | 250°–400° C. |
| VO$_2$ + Ag-based gas sensor | 300°–400° C. |
| ZnO + Pd-based gas sensor | 350°–450° C. |
| Fe$_3$O$_4$-based gas sensor | 350°–450° C. |
| SnO$_2$-based gas sensor | 350°–450° C. |

Thus, in the following Example, an integrated gas detection device is used, and thus 400° C. is used as the common heating temperature. For example, the sheet form heater is provided on the same side of the substrate as that at which gas sensors are provided through an electrically insulating layer to obtain a good temperature distribution and a good heating efficiency for the integrated configuration. The sheet form heater can be provided at the opposite side of the substrate, as shown in FIG. 4(b).

Sensitivity as characteristic value of a sensor, which shows the gas selectivity of a sensor for said gas components, is shown in the following Table 2.

TABLE 2

| Sensor No. | Sensitivity (V/ppm) | | | | | |
| --- | --- | --- | --- | --- | --- | --- |
| | O$_2$ | H$_2$ | NO$_2$ | CO | H$_2$O (vapor) | Hydrocarbon |
| 401 | 7.7 × 10$^{-4}$ | 0 | 0 | 0 | 1.8 × 10$^{-4}$ | 1.1 × 10$^{-4}$ |
| 402 | 0 | 1.6 × 10$^{-3}$ | 8.3 × 10$^{-4}$ | 2.3 × 10$^{-4}$ | 0 | 0 |
| 403 | 1.4 × 10$^{-3}$ | 0 | 0 | 0 | 0 | 0 |
| 404 | 0 | 1.7 × 10$^{-3}$ | 0 | 1.4 × 10$^{-3}$ | 0 | 0.2 × 10$^{-3}$ |
| 405 | 0 | 0.6 × 10$^{-3}$ | 0 | 1.3 × 10$^{-3}$ | 0 | 1.6 × 10$^{-3}$ |
| 406 | 0 | 0 | 0 | 0 | 1.5 × 10$^{-3}$ | 0 |

An example of analyzing a sample gas mixture containing 6 kinds of gas components (n=6) by a gas detection device according to the present invention will be given below.

Detected voltages generated at the same time by gas components of a sample mixed gas, that is, oxygen, hydrogen, nitrogen dioxide, carbon monoxide, water vapor, and hydrocarbon, by the individual sensors in the sensor section of the gas detection device are calculated by using a detection circuit including signal processing (not shown in Figure) and have the following values, where sensor number: detected voltage are given.

401: 3.79 V, 402: 2.63 V, 403: 5.60 V
404: 3.40 V, 405: 3.30 V, 406: 4.50 V

Hereinafter, values in voltage will be used as an acceptable value.

Suppose the concentrations of the respective gas components are represented by $X_{O2}$, $X_{H2}$, $X_{NO2}$, $X_{CO}$, $X_{H2O}$, and $X_{CmHn}$, respectively, in ppm unit, the following 6 simultaneous linear equations can be obtained by using voltage values as accepted values and utilizing the constants shown in Table 2.

$7.7 \times 10^{-4} \cdot X_{O2} + 0 \cdot X_{H2} + 0 \cdot X_{NO2} + 0 \cdot X_{CO}$
$\quad + 1.8 \times 10^{-4} \cdot X_{H2O} + 1.1 \times 10^{-4} \cdot X_{CmHn}$
$\quad = 3.79 - (1)$
$0 \cdot X_{O2} + 1.6 \times 10^{-3} \cdot X_{H2} + 8.3 \times 10^{-4} \cdot X_{NO2}$
$\quad + 2.3 \times 10^{-4} \cdot X_{CO} + 0 \cdot X_{H2O} + 0 \cdot X_{CmHn}$
$\quad = 2.63 - (2)$
$1.4 \times 10^{-3} \cdot X_{O2} + 0 \cdot X_{H2} + 0 \cdot X_{NO2} + 0 \cdot X_{CO}$
$\quad + 0 \cdot X_{H2O} + 0 \cdot X_{CmHn}$
$\quad = 5.60 - (3)$
$0 \cdot X_{O2} + 1.7 \times 10^{-3} \cdot X_{H2} + 0 \cdot X_{NO2} + 1.4 \times 10^{-3} \cdot X_{CO}$
$\quad + 0 \cdot X_{H2O} + 0.2 \times 10^{-3} \cdot X_{CmHn}$
$\quad = 3.40 - (4)$
$0 \cdot X_{O2} + 0.6 \times 10^{-3} \cdot X_{H2} + 0 \cdot X_{NO2} + 1.3 \times 10^{-3} \cdot X_{CO}$
$\quad + 0 \cdot X_{H2O} + 1.6 \times 10^{-3} \cdot X_{CmHn}$
$\quad = 3.30 - (5)$
$0 \cdot X_{O2} + 0 \cdot X_{H2} + 0 \cdot X_{NO2} + 0 \cdot X_{CO} + 1.5 \times 10^{-3} \cdot X_{H2O}$
$\quad + 0 \cdot X_{CmHn} = 4.50 - (6)$ By solving the foregoing simultaneous equations by computing means (not shown in FIG. 4), the following values are obtained as the concentrations of the individual gas components:

$X_{O2}$: 4.0 × 10$^3$, $X_{H2}$: 1.0 × 10$^3$, $X_{NO2}$: 1.0 × 10$^2$
$X_{CO}$: 1.0 × 10$^3$, $X_{H2O}$: 3.0 × 10$^3$, and
$X_{CmHn}$: 1.5 × 10$^3$ (Unit: ppm)

Figure 11:
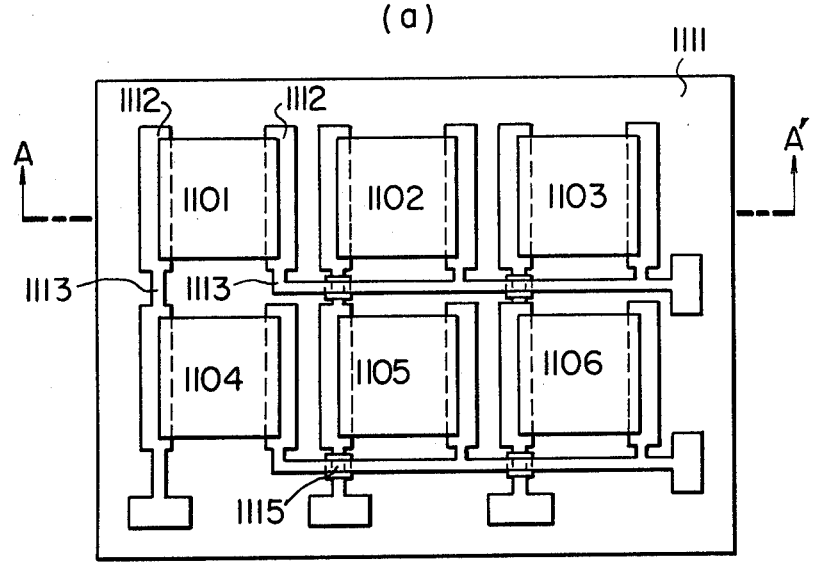
FIGS. 11(a) and (b), 12(a) and (b) and 13(a) and (b) are schematic structural views of other embodiments of gas detection devices according to the present invention.
Figure 11:
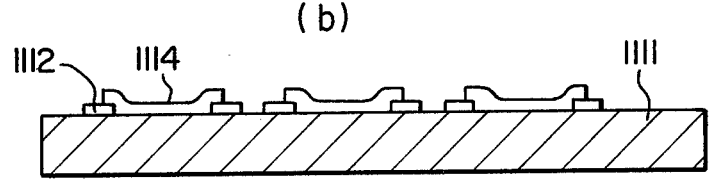

FIG. 11(a) schematically shows a second embodiment of the present invention, where a top surface structure of a sensor section of the present gas detection device is shown. FIG. 11(b) is a schematic cross-sectional view along the line A—A' of FIG. 11(a). As is obvious from FIGS. 11(a) and (b), 6 sensors 1101, 1102, 1103, 1104, 1105 and 1106 are arranged in a matrix configuration in the second embodiment, and the sensor surface is in a sheet configuration and is exposed to a sample gas. The individual electrodes are connected to one another in the line group or at the row group as shown in the first embodiment of the present invention, and the intersections of connectors between the electrodes are electrically insulated by a cross-over material.

The procedure for fabricating the device according to the second embodiment is substantially equal to that for the first embodiment. At first, electrodes 1112 and connectors 1113 between the electrodes are formed on a heat-resistant insulating substrate 1111 by using a gold conductor paste (for example, DuPont No. 8760) according to the well known thick film printing process. Then, gas sensor layers 1114 are formed from different kinds of sensor pastes, as in the first embodiment, for the individual sensors. At the intersections of the conductors between the electrodes, cross-over insulating layers 1115 are formed from a crystal glass paste (for example, DuPont No. 9429) on the first conductors by printing, and then second conductors are printed on the insulating layers. Then, the entire substrate is fired at the predetermined temperature to obtain the gas detection device according to the second embodiment.

Detected outputs from the individual sensors 1101–1106 of the second embodiment for the respective gas components of a sample mixed gas can be rapidly obtained. That is, concentrations of the respective gas components can be quantitatively determined as rapidly as that in the first embodiment.

Figure 12:
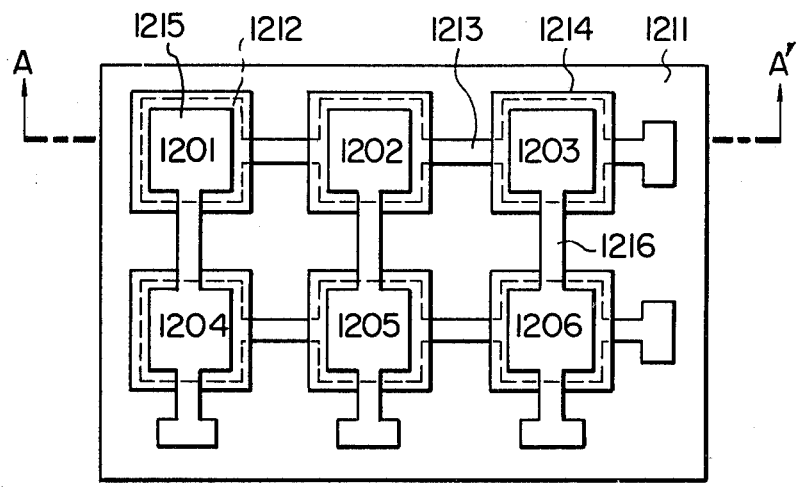
Figure 12:
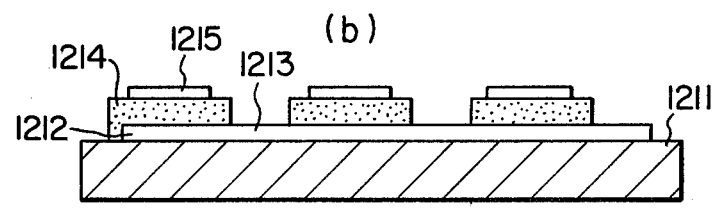

FIG. 12(a) shows a third embodiment of the present gas detection device of six sensors in the same sandwich configuration as in the first embodiment, except that only connector wirings for taking out the detected outputs are different from those of the first embodiment. FIG. 12(b) is a schematic cross-sectional view of the third embodiment along the line A—A of FIG. 12(a).

Figure 13:
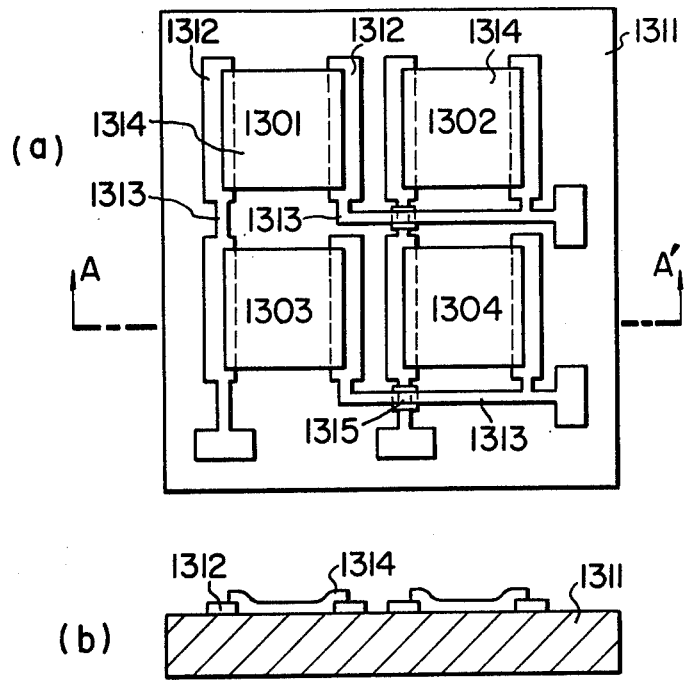

FIG. 13(a) shows a fourth embodiment of the present gas detection device, where the top surface structure of sensor section consisting of 4 sensors in the same sheet form as in the second embodiment for detecting 4 gas components is shown, and FIG. 13(b) is a schematic cross-sectional view of the fourth embodiment along the line A—A of FIG. 13(a). The gas detection device of the fourth embodiment is manufactured as follows: gold electrodes 1312 and connectors 1313 between the electrodes are formed on a glass substrate 1311 by masking-vapor deposition, and then gas sensor layers 1314 are formed on the electrodes for the individual sensors by sputtering process. Materials for the individual sensor layers 1314 are CoO for sensor 1301, ZnO+Pd for sensor 1302, $Fe_3O_4$ for sensor 1303, and $SnO_2$ for sensor 1304. In forming the electrodes, insulating layers 1315 of $SiO_2$ film are formed on the first conductors 1313 between the electrodes at the intersections of the conductors between the electrodes by sputtering process. Then, the second electrodes and connectors between the second electrodes are formed thereon by masking-vapor deposition. Then, an integrated circuit is provided at the device to amplify the detected voltage as signals.

In the wirings according to the second, third, and fourth embodiments, voltages from the individual sensors can be detected by successively selecting common buses in the line group and in the row group. The contributions of the individual gas components to the detected voltages can be computed according to the same procedure as that for the first embodiment.

In computing voltages as signals, a microprocessor can be provided (though not shown in Figure) to obtain concentration of the individual gas components at the final stage in real time.

Figure 14:
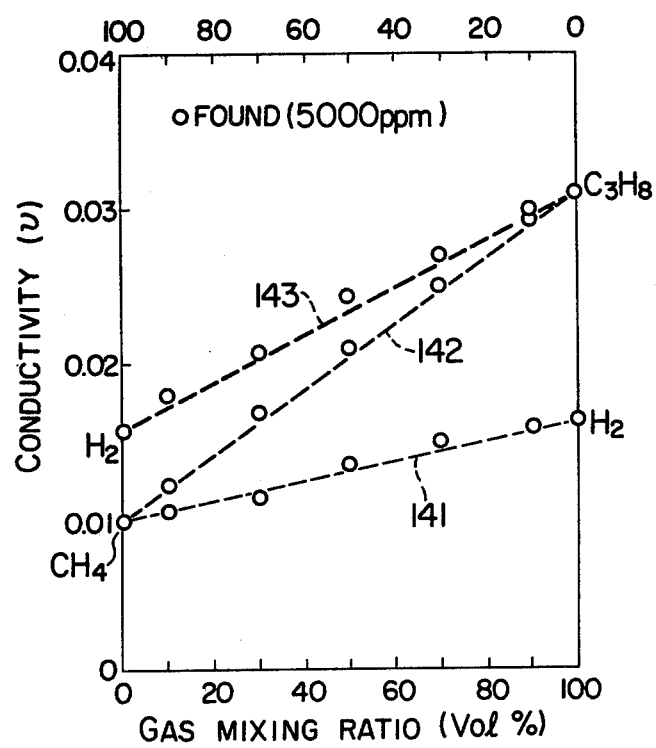
FIG. 14 is a diagram showing the additive nature of conductivity for gas concentrations of various mixed gases of $CH_4$—$H_2$ system, $CH_4$—$C_3H_8$ system, and $C_3H_8$—$H_2$ system, actually measured according to the gas detection device of the present invention.

FIG. 14 is a diagram showing the additivity as the basis for the technical concept of the present invention relating to the simplest binary mixed gases, that is, $CH_4$—$H_2$, $CH_4$—$C_3H_8$, and $H_2$—$C_3H_8$, where various values of electrical conductivity of the sensor element 404 determined from the detected voltages are shown with respect to various ratios between the two components of each gas mixture. The use of conductivity as a displayed value for the gas concentration is a result of the studies made by the present inventors to find that the conductivity can also maintain the additivity of gas concentration as displayed value. For example, the resistivity cannot maintain such simple additivity as displayed value. This is also a very important finding.

In the foregoing embodiments, alumina substrate ($Al_2O_3$) are used as heat-resistant insulating substrates 411, 1111, 1211 and 1311. Similar results can be obtained from insulating substrate materials shown in the following Table 3.

TABLE 3

| Other insulating substrate materials | |
| --- | --- |
| Forsterite | $2MgO.SiO_2$ |
| Steatite | $MgO.SiO_2$ |
| Mullite | $3Al_2O_3.2SiO_2$ |
| Silicon carbide | SiC |
| Zirconia | $ZrO_2$ |
| Spinel | $MgO.Al_2O_3$ |
| Berylia | BeO |

In the foregoing gas detection device according to the present invention, a gas sensor section has such a structure that a plurality of sensors comprised of gas sensor materials having different gas selectivities to specific gas components of a mixed gas are provided on an insulating substrate. The gas selectivity to specific gas components of a mixed gas can be obtained not only by using different sensor materials as described in the foregoing embodiments, but also by changing the process or process conditions in fabricating the sensor using the same material. It is also possible to integrate the sensors on a substrate of any suitable material insulated from the sensors. These modifications can be obvious to those skilled in the art from the disclosure of the foregoing embodiments without further illustration of embodiments.

The gas information thus obtained can be utilized in the following manner:

(1) Concentration of the individual gas components, or only desired gas components, can be obtained as outputs in a display device, such as meter, or in graph or numerical values.

(2) For example, a ratio of $CO/CO_2$ can be obtained as an output.

(3) Presence of specific gas components can be obtained as an output. In this case, the presence is simply made known by a buzzer.

As described above, the present gas detection device for analyzing a plurality of gas components can rapidly separate and quantitatively determine the individual gas components of a sample mixed gas with high accuracy.

Furthermore, a heater as well as a signal processing circuit can be provided on the same substrate by printing process (thick film process), and thus a simple and low cost gas analyzer as a sensor device for analyzing a plurality of gas components by signal processing in real time can be provided according to the present invention. The present invention can provide a remarkable effect in the relevant field.

What is claimed is:

1. A gas detection device for detecting concentration of any one of predetermined different gases in a gas mixture, said device comprising a substrate, a plurality of gas adsorbing sensors formed on said substrate, each of said sensors having different gas selectivities to the gases in the gas mixture, the number of said sensors being equal to the number of the different gases to be detected, at least two sensors being sensitive to at least two gases but having different sensitivities to said at least two gases, and each of said sensors adapted to provide an output having one or more output components, each component having a dimension of electrical conductivity and being proportional to the concentration of one of said different gases within a predetermined range of temperature of the sensor, said output of each sensor being the sum of said one or more output components, and means for computing the gas concentration of said any one of predetermined different gases using the outputs of said sensors produced at a temperature within said range.

2. The gas detection device according to claim 1, wherein the gas selectivities of the gas sensors to the known gas components are effected by utilizing different kinds of gas sensor materials for the different gas sensors.

3. The gas detection device according to claim 1, wherein the gas selectivities of the gas sensors to the known gas components are effected by using different conditions for fabricating gas sensor materials for the different gas sensors.

4. The gas detection device according to claim 1, wherein the gas selectivities of the gas sensors to the known gas components are effected partly by using different kinds of gas sensor materials for the different gas sensors and partly by using different conditions for fabricating gas sensor materials for the different gas sensors.

5. The gas detection device according to claim 1, further comprising a heater for heating the gas sensors to their operating temperature, and wherein the heater is a sheet form heater.

6. The gas detection device according to claim 5, wherein the heater is provided on one side of said substrate and the gas sensors are provided on the other side.

7. The gas detection device according to claim 6, wherein the heater includes means for heating and maintaining the gas sensors at 400°–450° C.

8. The gas detection device according to claim 1, wherein the gas sensors are arranged in a matrix configuration.

9. The gas detection device according to claim 8, wherein output terminals of the gas sensors in the matrix configuration are in a structure in which one of the output terminals of each gas sensor belonging to a line group of the matrix configuration is connected to a common electrode, and other output terminals of the gas sensors are open, and are scanned, thereby providing said output individually.

10. The gas detection device according to claim 8, wherein output terminals of the gas sensors in the matrix configuration are in a structure in which one of the output terminals of each gas sensor belonging to a line group of the matrix configuration is connected to a common electrode, and the other output terminals of gas sensors belonging to a row group of the matrix configuration are connected to another common electrode, thereby providing said output by selecting a common electrode to the line group and a common electrode to the row group.

11. The gas detection device according to claim 5, wherein the heater and gas sensors are provided on one side of said substrate, said heater being separated from said gas sensors by an electrically insulating layer.

12. The gas detection device according to claim 11, wherein the heater includes means to heat and maintain said gas sensors at 400°–450° C.

13. The gas detection device according to claim 12, wherein the gas sensors are arranged in a matrix configuration.

14. The gas detection device according to claim 13, wherein output terminals of the gas sensors in the matrix configuration are in a structure in which one of the output terminals of each gas sensor belonging to a line group of the matrix configuration is connected to a common electrode, and other output terminals of the gas sensors are open, and are scanned, thereby providing output individually.

15. The gas detection device according to claim 13, wherein output terminals of the gas sensors in the matrix configuration are in a structure in which one of the output terminals of each gas sensor belonging to a line group of the matrix configuration is connected to a common electrode, and the other output terminals of gas sensors belonging to a row group of the matrix configuration are connected to another common electrode, thereby providing said output by selecting a common electrode to the line group and a common electrode to the row group.

16. The gas detection device according to claim 1, wherein said output provided by each of said sensors and used in the computing means is an output voltage of each sensor.

17. The gas detection device according to claim 16, wherein said means for computing comprises means for solving n simultaneous equations as follows:

$$Pi = \sum_{j=1}^{n} a_{ij} X_j$$

$$(i = 1, 2 \ldots m)$$

wherein
Pi=detected output voltage generated by total gas components from sensor i;
m=number of gas sensors;
n=number of gas components in a sample gas;
Xj=concentration of specific gas component j; and
αij=sensitivity of sensor i to specific gas component j, a constant value.

18. A method for detecting concentration of any one of predetermined different gases in a gas mixture, utilizing a plurality of gas adsorbing sensors equal in number to the number of the different gases to be detected, each of the gas sensors having a different gas selectivity, at least two sensors being sensitive to at least two gas components but having different sensitivities to said at least two gas components, which comprises detecting an output voltage of each of the individual gas sensors having different gas selectivities, and computing the concentration of any one of the predetermined different gases from the detected output voltages by solving the n simultaneous equations:

$$Pi = \sum_{j=1}^{n} a_{ij} X_j$$

$$(i = 1, 2, \ldots m)$$

wherein
Pi: detected output voltages generated by total gas components from sensor i,
m: number of gas sensors,
n: number of gas components in a sample gas,
Xj: concentration of specific gas component j, $a_{ij}$: sensitivity of sensor i to specific gas component j, a constant value.

19. The method according to claim 18, wherein the presence of a specific gas component is indicated by a buzzer alarm.

20. The method according to claim 18, wherein the ratios of a plurality of specific gas components are computed.

21. The method according to claim 18, wherein the gas concentration is displayed by a display device.

* * * * *

UNITED STATES PATENT AND TRADEMARK OFFICE
CERTIFICATE OF CORRECTION

PATENT NO. : 4,457,161
DATED      : July 3, 1984
INVENTOR(S): Shoichi IWANAGA et al It is certified that error appears in the above-identified patent and that said Letters Patent is hereby corrected as shown below:

```
First page of the patent, left-hand column, line 2
     of Item "[75]", delete "Isegami" and insert
     therefor -- Ikegami --;

First page of the patent, left-hand column, line 1
     of Item "[22]", delete "1981" and insert
     therefor -- 1982 --; and First page of the patent, left-hand column, delete
     Item "[30]" in its entirety.
```

Signed and Sealed this

Twenty-fifth Day of June 1985

[SEAL]

*Attest:*

DONALD J. QUIGG

*Attesting Officer*   *Acting Commissioner of Patents and Trademarks*